United States Patent [19]

Nelson et al.

[11] Patent Number: 4,978,662
[45] Date of Patent: Dec. 18, 1990

[54] 2-SUBSTITUTED TRIMETHYLPYRAZINE DERIVATIVES AS INHIBITORS OF PLATELET FUNCTION

[75] Inventors: Mark L. Nelson, Sommerville, Mass.; Peter H. Doukas, Newtown; Leon Salganicoff, Philadelphia, both of Pa.; Fiore J. Ricciardi, Milwaukee, Wis.

[73] Assignee: Temple University of the Commonwealth System of Higher Education, Philadelphia, Pa.

[21] Appl. No.: 336,261

[22] Filed: Apr. 11, 1989

[51] Int. Cl.$^5$ ............... A61K 31/495; A61K 31/335; C07D 241/12
[52] U.S. Cl. .................. 514/235.8; 514/252; 514/255; 544/336; 544/357; 544/359
[58] Field of Search ............... 544/120, 336, 357, 360, 544/359; 514/252, 255, 235.8

[56] References Cited

U.S. PATENT DOCUMENTS 4,620,004 10/1986 Sanders et al. ................... 544/357

OTHER PUBLICATIONS

Yang, Chu-Yao, *Chemical Abstracts*, 95(15): 132813p, p. 667, Oct. 12, 1981.

Joshi, S. C., *Chemical Abstracts*, 99(11): 88170h, p. 569, Sep. 12, 1983.

Ohta, Akihiro, *Chemical Abstracts*, 102(1): 6421j, p. 584, Jan. 7, 1985.

*Chemical Abstracts Registry Handbook*, 1981 Supplement, 79074-40-1.

*Primary Examiner*—Mary C. Lee
*Assistant Examiner*—Jacqueline Haley
*Attorney, Agent, or Firm*—Seidel, Gonda, Lavorgna & Monaco

[57] ABSTRACT

Novel 2-substituted trimethylpyrazine derivatives of the formula:

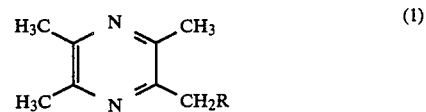

wherein R is alkylamino, 4-methyl-1-piperazinyl, piperidino, morpholino or 2-trimethylpyrazinepropenyl.

These novel 2-substituted trimethylpyrazine derivatives exhibit, at very low concentrations, activity as inhibitors of platelet function and as promoters of blood pressure reduction.

22 Claims, 11 Drawing Sheets

2-SUBSTITUTED TRIMETHYLPYRAZINE DERIVATIVES AS INHIBITORS OF PLATELET FUNCTION

FIELD OF THE INVENTION

This invention relates generally to 2-substituted trimethylpyrazine derivatives having platelet function inhibition and blood pressure reduction activity.

BACKGROUND OF THE INVENTION

It is known that the administration of certain compounds containing a pyrazine ring as a main nucleus inhibit blood platelet function, i.e. platelet aggregation. However, the activity of these compounds is too weak for effective platelet aggregation inhibition.

The inhibition of platelet function by tetramethylpyrazine is disclosed in Ka Kit Nui et al., *Res. Comm. Chem. Pathol. and Pharmacol.*, 58, 3–14 (1987).

U.S. Pat. No. 4,123,613 discloses substituted pyrazine derivatives exhibiting activity as inhibitors of platelet aggregation. They are prepared by condensing 10-methoxy-16-dimethylergoline-8-beta-methanol tosylate with the sodium salt of a mercaptopyrazine or aminopyrazine.

U.S. Pat. No. 4,721,713 discloses a method of platelet aggregation inhibition by administering 2-hydroxy-3-isopropyl-5,6-dimethylpyrazine or a hydrate thereof.

Japanese Patent Application No. 88-025709 discloses 2-alkoxy-3,5,6-substituted-pyrazine derivatives useful in inhibiting platelet aggregation and promoting vasodilation.

Japanese Patent Application No. 88-053935 discloses 2,3-di:phenyl-5-benzyl-pyrazine derivatives useful in inhibiting platelet agglutination and the prevention of diseases caused by platelet agglutination.

European Patent Application No. 194,686 discloses the preparation and use of dihydropyrazine derivatives having platelet aggregation-inhibiting activity.

None of the references teach the compounds of the present invention.

SUMMARY OF THE INVENTION

The invention provides novel 2-substituted trimethyl pyrazine derivatives of the formula:

wherein R is selected from alkylamino, 4-alkyl-1-piperazinyl, piperidino, morpholino and 2-trimethylpyrazinealkenyl.

As a result of extensive studies, it has been found that the novel 2-substituted trimethylpyrazine derivatives possess, at very low concentrations, potent platelet aggregation-inhibiting activity and blood pressure reduction activity.

The invention, therefore, provides a method for inhibiting blood platelet aggregation in mammals by administering to such a mammal an effective amount of a compound of formula (I). The invention, also, provides a method for promoting blood pressure reduction in mammals by administering to such a mammal an effective amount of a compound of formula (I).

DESCRIPTION OF FIGURES

FIGS. 15 (*a–c*) are a set of blood pressure tracings of male Wistar rats depicting hemodynamic fluctuations in the presence of 1,3-bis-(2-trimethylpyrazinyl)propene.

DETAILED DESCRIPTION

In accordance with the present invention there are provided novel 2-substituted trimethylpyrazine derivatives having the above-mentioned formula (I) wherein R is selected from alkylamino, 4-alkyl-1-piperazinyl, piperidino, morpholino and 2-trimethylpyrazinealkenyl. These novel compounds may be prepared from tetramethylpyrazine ("TMPZ") (available from Aldrich Chemical Co., Inc., Milwaukee, Wisconsin).

The alkylamino, 4-alkyl-1-piperazinyl, piperidino and morpholino compounds of the invention are prepared by refluxing TMPZ with N-chlorosuccinimide to form chloromethyltrimethylpyrazine. The chloromethylpyrazine is reacted with an alkylamine, 4-alkyl-1-piperazine, piperidine or morpholine to form the corresponding 2-substituted trimethylpyrazine derivative of the invention.

The 1,3-bis-(2-trimethylpyrazinyl)propene compound of the invention may be prepared by condensing 2,3,5,6-tetramethylpyrazinylanion (prepared by reacting TMPZ with phenyllithium) with ethylformate in the presence of diethyl ether ($Et_2O$).

The present invention will be illustrated in more detail by reference to the following non-limiting examples.

EXAMPLE 1

3,5,6-Trimethylpyrazinylmethyl-n-pentylamine

A reaction mixture containing N-chlorosuccinimide (6.67 g, 50.0 mmol), benzoylperoxide (50 mg) and TMPZ (6.81 g, 50.0 mmol), in 125 ml of reagent grade $CCl_4$ was refluxed for 12 hours. The reaction solution was then cooled to 0° C. and filtered, removing succinimide. The solvent was evaporated in vacuo resulting in an oil (chloromethyltrimethylpyrazine). The oil was cooled to 0° C. and 25 ml of distilled n-amyl amine was dripped into the oil over a 20 minute period. The reaction mixture was stirred in an ice bath until an exothermic reaction ensured whereby the mixture was gently refluxed for 5 hours. Upon filtration of this reaction mixture, the resulting oil was chromatographed by flash column chromatography using 230-400 mesh silica gel (available from Fisher Scientific Co., King of Prussia, Pa.). Fractional separation was obtained by using a gradient solvent system (100% $CHCl_3\rightarrow25:1$ $CDCl_3/MeOH+1\%$ $NH_4OH$). Purification by Kugelrohr distillation at 90° C./15 mm Hg afforded 15% yield of a clear oil. m.p. 174°-175° C. Analysis: H-NMR($CDCl_3$) (ppm): 3.8(2H,S), 2.6-2.7(2H,t), 2.45-2.5(9H,t), 1.8-1.9(2H,m), 1.5-1.6(2H,m), 1.3-1.37(4H, sextet), 0.8-0.9(3H,t).

EXAMPLE 2

2-Melhylene (4'-methylpiperizanyl-1')-3,5,6-trimethylpyrazine

A solution of N-methylpiperazine (4.07 g, 40.0 mmol) in 50 ml of dry $Et_2O$ was dripped slowly into 3.71 g (22.0 mmol) chlormethyltrimethylpyrazine prepared according to Example 1. After stirring in an ice bath, the solution is stirred for two hours and then refluxed for 1 hour. After cooling, the solid precipitant was filtered off leaving a yellow oil. The oil was chromatographed by the flash chromatography procedure utilized in Example 1. The chromatography procedure resulted in a 32.7% yield of a viscous product. m.p. 196° C.

Analysis: H-NMR($CDCl_3$) (ppm): 3.5-3.9(6H,m), 2.5-2.6(9H,t), 2.4(3H,S), 2.3-2.4(4H,m).

EXAMPLE 3

2-Methylene (piperidinyl-1')-3,5,6-trimethylpyrazine 3.71 g (22.0 mmol) of chloromethyltrimethylpyrazine, as prepared in Example 1, was condensed with 3.9 g (40.0 mmol) of distilled piperidine. After filtration to remove excess piperidine HCl, the resulting oil was distilled at 110° C./0.5 mm Hg, resulting in a 36.7% yield of a light yellow oil. Further purification of this product was obtained by the flash chromatography procedure utilized in Example 1. m.p. 210°-213° C.

Analysis: Mass Spectrum m/e (% relative abundance): 219(13.1)M+, 135(100), 84(37).

H-NMR ($CDCl_3$) (ppm): 3.6(2H,S), 3.5-3.6(9H,d), 2.2(4H,S), 1.4-1.6(6H,br m).

EXAMPLE 4

2-Methylene (morpholine-1')-3,5,6-trimethylpyrazine 3.71 g (22.0 mmol) of chloromethyltrimethylpyrazine, as prepared in Example 1, is condensed with 3.90 g (40.0 mmol) of distilled morpholine. After filtration to remove excess morpholine HCl, the solvent was removed in vacuo resulting in a viscous oil. Further purification of this product was obtained by the flash chromatography procedure utilized in Example 1. The chromatography procedure resulted in a 23.0% yield of the isolated product. m.p. 204°-206° C.

Analysis: Mass Spectrum m/e (% relative abundance): 221(4)M+, 135(100), 86(3.5).

H-NMR($CDCl_3$) (ppm): 3.6(6H,m), 2.5-2.6 (13H,m).

EXAMPLE 5

1,3-Bis-(2-trimethylpyrazinyl)propene 9.25 ml of a 2.7M solution of phenyllithium (in cyclohexane) was added to a flask which was cooled to 0° C. in an ice bath. 30 ml of a 7:3 solution of benzene/$Et_2O$ was added to the flask. The resulting solution was cooled to 0° C. 3.4 grams (24.9 mmol) of TMPZ, dissolved in 25 ml of benzene/$Et_2O$ (7:3), was slowly added, over a 30 minute period, dropwise into the phenyllithium solution while stirring at 0° C. The solution was then stirred for 2 hours and gently refluxed for 1 hour. The formation of the pyrazinyl-lithioanion (2,3,5,6-tetramethylpyrazinyl anion) was evidence by the formation of a brilliant red solution. 3.0 g (22.0 mmol) of 2,3,5,6-tetramethylpyrazinyl anion was condensed with 0.85 g (11.0 mmol) of distilled ethyl formate which was dissolved in an equal amount of $Et_2O$. After the reaction mixture had refluxed for 2.5 hours and cooled to 0° C., 30 ml of distilled water was added. The resulting organic layer was separated and dried over sodium sulfate. The organic phase was filtered and concentrated in vacuo to produce a yellow oil. The oil was chromatographed by flash chromatography using 230-700 mesh silica and a gradient solvent system (100% $CHCl_3\rightarrow25:1$ $CHCl_3/MeOH$) which resulted in several fractions. Upon filtration of the aqueous layer, a white crystalline solid was obtained at a 26.1% yield. Recrystallization in acetone-$H_2O$ system afforded pure white plates. m.p. 63°-65° C. (free base); 212°-214° C. (HCL salt).

Analysis: Mass Spectrum m/e (% relative abundance): 282 (55.7) M+, 267(54), 161(100).

H-NMR(CDCl$_3$) (ppm): 6.95–7.01(1H,m), 6.59–6.64(1H,d), 3.95–4.10(2H,br d), 2.33–2.60(18H, sextet).

Inhibitory Effect on Blood Platelet Aggregation

Venous blood was collected from the antecubital vein of human volunteers who were aspirin-free for at least one week and possessed hematocrit in acceptable ranges (men, 40–54%; women, 37–47%). The participants were recruited through the Specialized Center for Thrombosis Research, Temple University School of Medicine, Philadelphia, PA. The blood was collected using a heparinized 16 gauge venotube, and placed into plastic centrifuge tubes containing 1/10th volume of 3.8% (w/v) trisodium citrate. Platelet-rich plasma (PRP) was prepared by centrifuging the citrated blood at 100 r.p.m. for 20 minutes at 25° C. Platelet-poor plasma (PPP) was prepared by centrifugation of PRP at 10,000 r.p.m. for 2 minutes.

Inhibitors of platelet aggregation were screened by the turbidimetric bio-assay method initially described by Born, G. V. R., *Nature*, 194, 927–929 (1962) using an Instech Laboratories Model 3000 Research Aggregometer coupled to a Hewlett Packard Model 680 strip chart recorder. Test compounds were dissolved in isotonic saline at concentration of 0.10M. Adenosine diphosphate (ADP) was dissolved in a saline solution at a concentration of 0.05M. Epinephrine hydrochloride was dissolved in a saline solution at a concentration of 0.0054M.

The amount of PRP used in each test cuvette was constant at 0.7 ml (platelet counts ranged from 2 to $6 \times 10^8$ platelets/ml as determined by Coulter Counter techniques). The volume of inhibitor solution added to the PRP was held constant to 10 $\mu$l. Control cuvettes received 10 $\mu$l of an isotonic solution.

The PRP was stirred at 950±/−10 r.p.m. at 37° C. for 2 minutes with the inhibitor prior to the addition of the aggregating agent. Changes in the optical density were analyzed corresponding to platelet aggregation waves. All inhibitor compounds of the invention were screened on 3 separate days using up to 1.4 mM of each compound of the examples.

Figure 1:
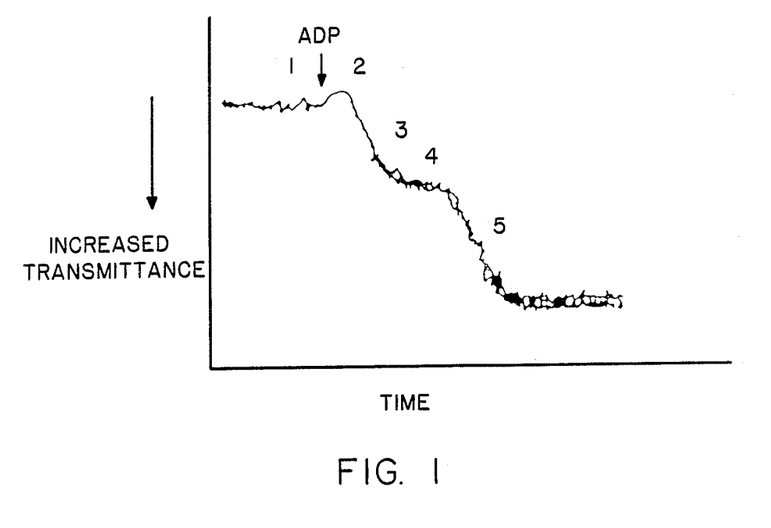
FIG. 1 is a profile of normal platelet aggregation pattern in response to the challenge of adenosine diphosphate (ADP).

Normally, PRP undergoes a complete response to ADP which includes both a primary and a secondary wave of platelet aggregation. A normal complete platelet aggregation pattern is presented in FIG. 1, which illustrates that primary (3) and secondary (5) waves of aggregation have different shapes.

Generally, compounds that inhibit primary aggregation also inhibit secondary aggregation. However, compounds that inhibit secondary aggregation do not necessarily affect primary aggregation.

PRP samples contain platelet concentrations that vary between donors. In order to normalize any potential differences in biological reactivity to ADP, individual suspensions may be titrated with small increments of ADP until an "end point" aggregation response is achieved, i.e., an aggregation response consisting of a sharp primary wave, a distinct reaction plateau, and a maximum secondary wave.

Figure 2:
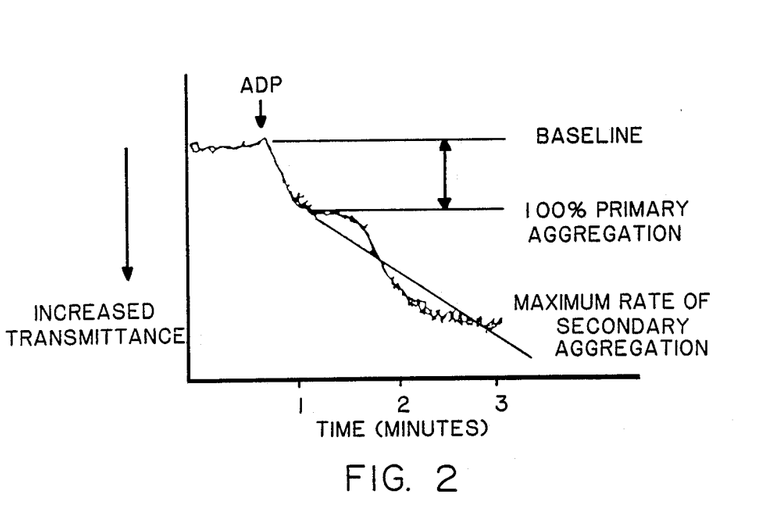
FIG. 2 is a profile of the measurement of the primary and secondary waves of platelet aggregation as endpoints in a bioassay, and illustrates the end-points utilized in assessing the activity of the pyrazine compounds.

FIG. 2 illustrates the end-point platelet aggregation responses utilized in assessing the activity of the pyrazine compounds. The primary and secondary waves are visible. The effect of the inhibitor compounds on primary aggregation were recorded as direct measurements (100% primary aggregation). The effects of the inhibitor compounds on secondary aggregation were recorded as the mean of the secondary aggregation slope (maximum rate of secondary aggregation).

Figure 3:
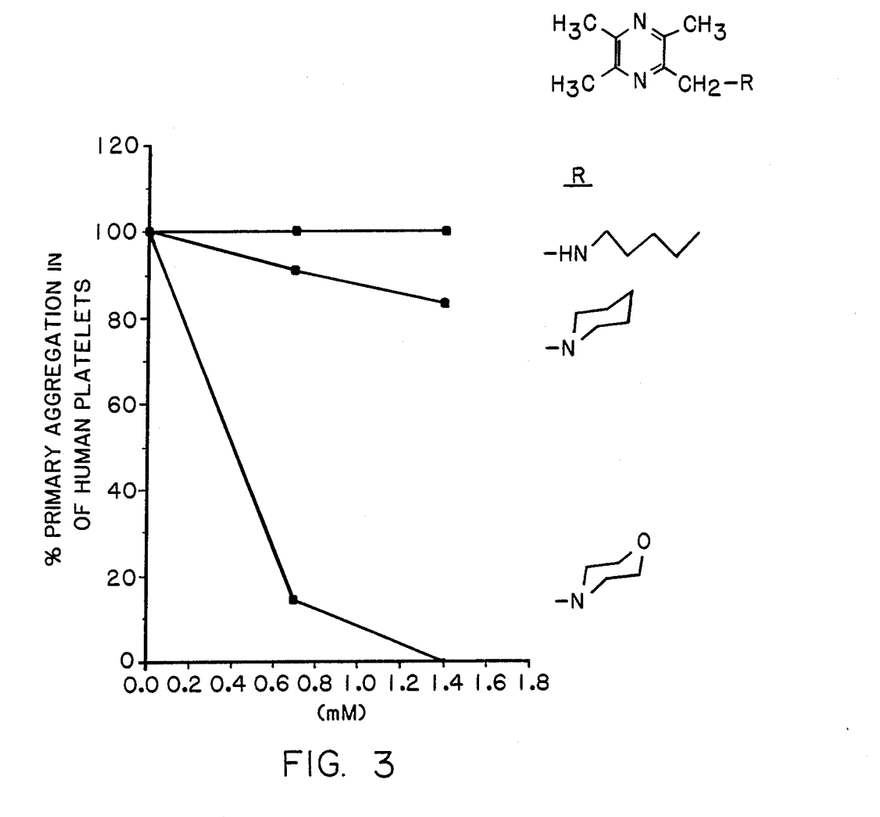
FIG. 3 is a graph showing the inhibition of primary aggregation of human platelets by 2-substituted trimethylpyrazine derivatives, utilizing adenosine diphosphate (ADP) as the aggregant.
Figure 4:
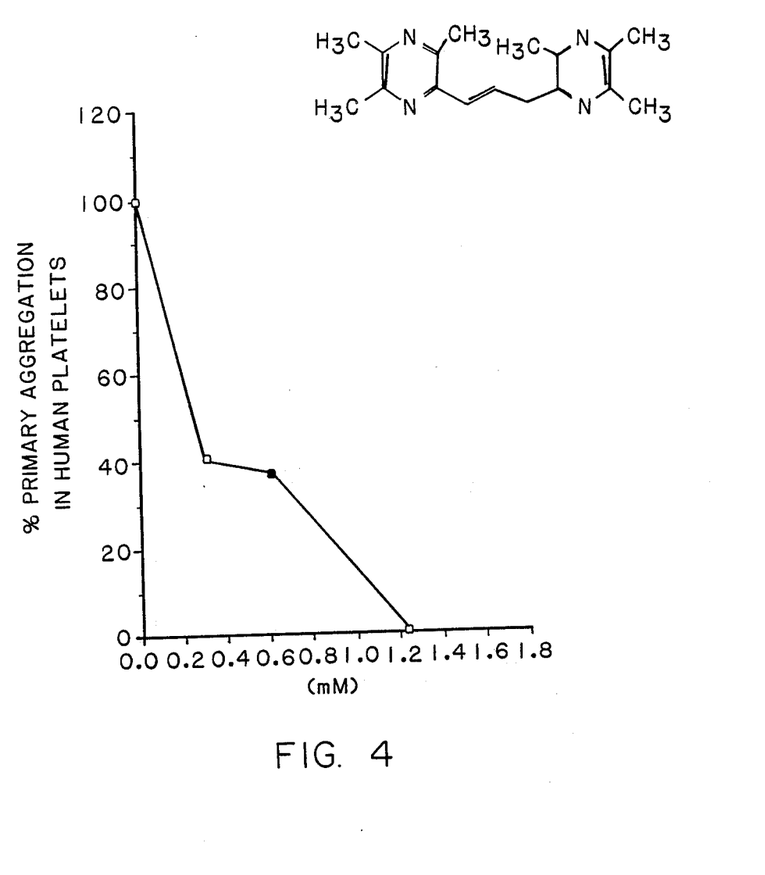
FIG. 4 is a graph showing the inhibition of primary aggregation of human platelets by 1,3-bis-(2-trimethylpyrazinyl)propene, utilizing ADP as the aggregant.
Figure 5:
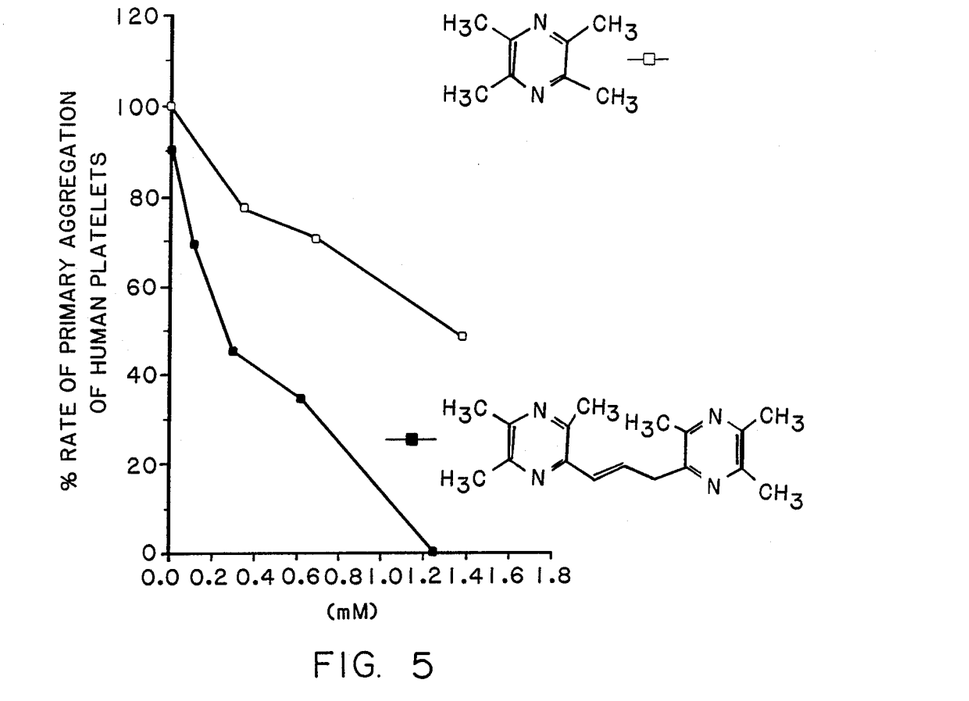
FIG. 5 is a graph showing the inhibition of primary aggregation of human platelets by TMPZ and 1,3-bis-(2-trimethylpyrazinyl)propene, utilizing epinephrine as the aggregant.

The extent of aggregation during the primary wave was measured three minutes after aggregant (e.g. ADP) addition (1.4–3.5 $\mu$M). The amount of ADP used was determined by prior titration to the reactive end point. No less than 3 observations at each of three inhibitor concentrations (0.35 mM, 0.70 mM, 1.40 mM) were performed and compared to the control (PRP with no inhibitor) tracings. The results are shown in FIGS. 3, 4 and 5. Utilizing ADP to induce an aggregation stimulus, the effect of the inhibitor compounds of Examples 1, 3 and 4 on primary aggregation in human platelets is represented as a percent of primary aggregation in FIG. 3. FIG. 4 shows the percent of primary aggregation of the inhibitor compound of Example 5 upon a 1.4 $\mu$M ADP challenge. FIG. 5 shows the percent rate of primary aggregation caused by TMPZ and 1,3-bis-(2-trimethylpyrazinyl)propene, as both are challenged by 7.7 $\mu$M of epinephrine. The compound of Example 5 exhibited a five-fold increase over TMPZ in the inhibition of primary aggregation induced by epinephrine. The aggregation experiments were generally performed within 1–3 hours from the time of blood collection to insure platelet response.

Figure 6:
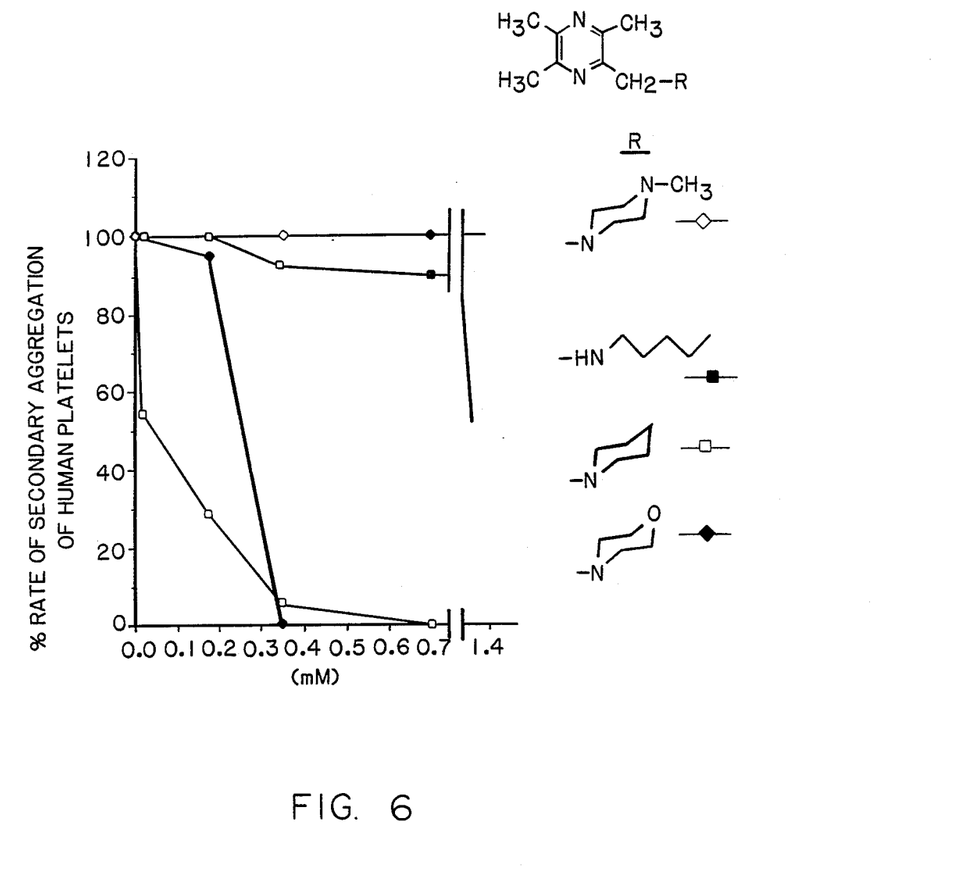
FIG. 6 is a graph showing the inhibition of secondary aggregation of human platelets by 2-substituted trimethylpyrazine derivatives, utilizing ADP as the aggregant.

The effect of the 2-substituted trimethylpyrazine derivatives on secondary aggregation rate is presented in FIG. 6. The extent of aggregation during the secondary wave was measured as the mean of the secondary aggregation slope for a minimum of three observations. The compound of Example 3 exhibited a significant increase in activity, demonstrating an IC$_{50}$ of 40 $\mu$M. The compound of Example 4 exhibited an IC$_{50}$ of 0.40 mM.

As shown in FIG. 3, the inhibitor compounds of Examples 3 and 4 inhibited primary aggregation at concentrations from about 0.7 mM to about 1.4 mM. However, the order of potency between the inhibitor compounds of Examples 3 and 4 was reversed in comparison to their inhibition of secondary aggregation.

Figure 7:
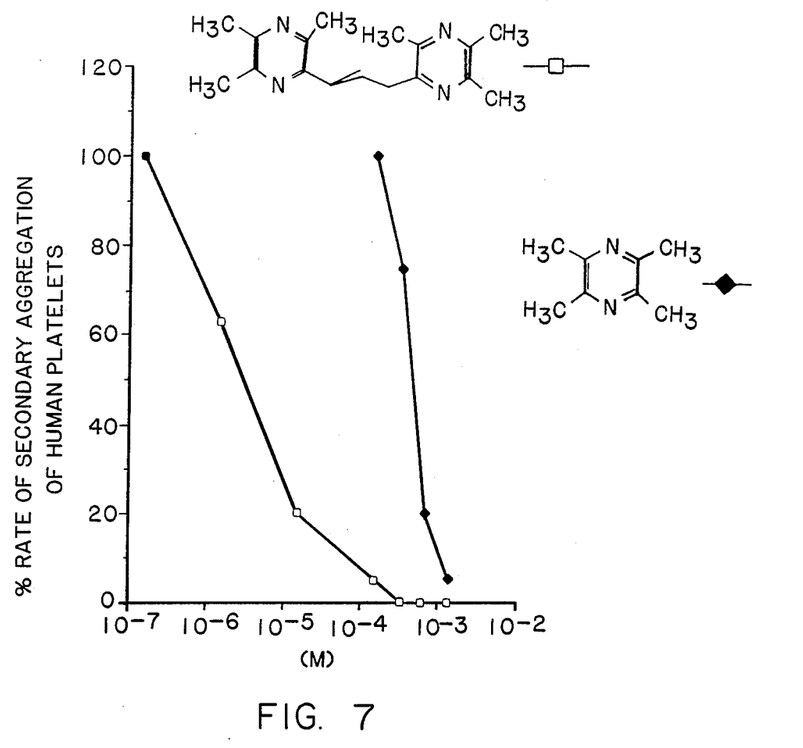
FIG. 7 is a graph showing the inhibition of secondary aggregation of human platelets by TMPZ or 1,3-bis-(2-trimethylpyrazinyl)propene, utilizing ADP as the aggregant.

The most potent platelet aggregation inhibitor tested was 1,3-bis-(2-trimethylpyrazinyl)propene (compound of Example 5). As illustrated in FIGS. 5 and 7, this compound demonstrated a several hundred-fold increase (IC$_{50}$ of $4.8 \times 10^{-6}$M) in inhibition of secondary aggregation as compared to TMPZ (see FIG. 7 which shows the percentage rate of secondary aggregation of human platelets by TMPZ and by the inhibitor compound of Example 5). The aggregation stimulus in FIG. 7 was induced by 1.4 $\mu$M of ADP for the compound of Example 5, and 4.2 $\mu$M of ADP for TMPZ.

The compound of Example 5 was able to completely abolish primary aggregation with an IC$_{50}$ of 0.28 mM (see FIG. 4).

Inhibitory Effect on Contractile Agonists

The platelet-strip technique described by Salganicoff, et al., *Am. J. Physiol.*, 249, 288 (1985), allows the direct measurement of contractile responses of thrombin-activated platelet aggregates. The platelet-strip behaves as a metabolically active contracting and relaxing aggregate, whose character is believed to parallel that of platelets undergoing secondary aggregation. The inhibitory effect of the 1,3-bis-(2-trimethylpyrazinyl)propene (Compound of Example 5) was tested against various platelet aggregates and contractile agonists, and compared to the inhibitory activity of the parent compound TMPZ, using the procedure as set forth below. Sections A, B, C, D and E describe the preparation of physiological solutions of the relevant antagonists and contractile agonists. These sections also describe the preparation of platelet solutions and methods for centrifugation and strip mounting. Sections F and G describe the procedure and discuss observations, respectively.

A. Solutions: (i) Modified Krebs-Henseleit (MK-H) solution: Prepared by dissolving 69.54 grams of NaCl (1.19M), 2.98 grams of KCl (0.04M), 4.07 grams of $MgCl_2$ (0.02M) and 1.63 grams of $KH_2PO_4$ (0.03M) in 700 ml of distilled water, and then q.s. the solution to 1 liter with distilled water.

MK-H Working Solution: 100 ml of the MK-H Solution was dissolved in 700 ml of distilled water. 2.1 g of $NaHCO_3$ (0.025M), 900 mg of glucose (0.005M) and 20 mg of Na-EGTA (sodium ethyleneglycol-bis(beta-aminoethylether-N,N'-tetraacetic acid; 50 $\mu$M) were added to the solution. The solution was then q.s. to 1 liter with distilled water. The calcium concentration was adjusted using 1.5M $CaCl_2$ solution. The final solution was gassed using 95% $O_2$-5% $CO_2$ to adjust the pH to 7.4.

The MK-H Working Solution is used as the bath medium in mounting the test platelet strips.

(ii) Krebs-Henseleit Depolarizing (K-HDP) Solution: Prepared by dissolving 98.46 grams of potassium sulfate (0.565M), 2.48 grams of magnesium sulfate (0.10M) and 12.5 grams of potassium hydrogen carbonate (0.125M) in 700 ml of distilled water and then q.s. to 1 liter with distilled water. The final solution was gassed using 95% $O_2$-5% $CO_2$ to adjust the pH to 7.4.

A 1/10th dilution of the K-HDP Solution is used to relax fully activated platelet strips.

B. Test Compounds: The compounds tested as contractile antagonists were dissolved in a saline solution at a concentration of 0.10M. Contractile agonists used were as 0.001M sodium arachidonate dissolved in dimethylsulfoxide; 0.05M adenosine diphosphate dissolved in a saline solution; 0.0054M epinephrine hydrochloride dissolved in a saline solution; 0.10M of $CaCl_2$ dissolved in a saline solution; and 0.001M of SQ-26655 (Squibb Institute of Medical Research, Princeton, N.J.) dissolved in 95% ethanol.

C. Platelet Isolation: Blood was collected from human donors in a method similar to that used in evaluating the inhibitory effect on blood platelet aggregation. However, the blood was transferred to a centrifuge tube containing 1/10 volume of a solution containing 2.5% sodium citrate, 1.5% citric acid and 2.0% dextrose (hereinafter "ACD solution"). PRP was prepared by isolating the supernatant obtained from centrifuging the ACD/blood solution at 1,000 r.p.m. for 20 minutes. The PRP, containing $9 \times 10^9$ platelet/ml, was neutralized and rapidly mixed with 4/100 of plasma volume of equal parts of 1.5M tris(hydroxymethyl)aminoethane-Cl, pH 7.4, and 0.5M $CaCl_2$. The centrifuge tube was immediately filled with recalcified PRP and centrifuged (at 10,000 r.p.m. for 10 minutes) onto the surface of a nylon mesh disc, thus trapping the platelets, forming a disc. The PPP was decanted and the tops of the tubes covered with a saline-dampened cotton. The tubes were incubated at 37° C. for 20 minutes. During this time the recalcified platelet pellet was fully activated by the thrombin formed in the residual plasma.

D. Preparation of Platelet-Strip: After activation, the disc containing the platelet aggregate was removed. The platelet disc was placed on a piece of plastic in cold MK-H Working Solution. A rectangular section was cut from the disc and experimental strips were prepared by cutting 4 mm wide strip sections. Each strip was calculated to contain approximately $7.4 \times 10^8$ platelets per strip (1.25 mg protein).

E. Mounting: Each individual strip was attached to a small plastic sheet and mounted in a 5.8 ml jacketed organ bath. The strips were connected to a plastic clip that was fastened with a gold chain to a transducer. The bottom of the strip was inserted into a clamp and the organ bath moved up carefully covering the top of the plastic clip with a bath solution of MK-H Workign Solution. A steady, slow, stream of 95% $O_2$/5% $CO_2$ was bubbled into the bath solution. The strip was floated in the bath solution at 5° C. for one hour. After this one hour period of equilibration at 5° C., a pre-load tension of 100 mg was applied to the strip as an initial tension. At this point, water at 37° C. was circulated through the outer jacket causing the platelet strips to contract by metabolic activation, achieving a force of 400–500 mg within about 30 minutes. Once fully activated, the strips were relaxed (tension is decreased across the platelet strip) by the K-HDP Solution. After 1 hour, the strips were placed in the MK-H Working Solution having no external CaH. CaH was then added slowly to a final concentration of 1 mM.

F. Procedure: After equilibrating to a resting tension, the strips are very sensitive to contractile agents and are ready for use in evaluating platelet contracting inhibitor activity. The testing procedure with the platelet strips involves the use of contractile agents either in the presence of an inhibitor compound or in the absence of the inhibitor compound (Control). The platelet strip assays are performed in a bath medium of the MK-H Working Solution at 37° C., containing $Ca^{2+}$ at a concentration of 50 $\mu$M or 1 $\mu$M. Prior to the initiation of a contractile agent, the bath solution containing the platelet strip and a specific concentration of the inhibitor compound of Example 5 is incubated for two minutes. When added to the bath medium, the contractile agents will restore part of the lost tension which produces a contractile response. The contractile activity is recorded isometrically using a Statham UC2 force transducer (or equivalent). The signal is amplified and fed into a data point recorder (i.e. Gould Multichannel recorder or equivalent).

Figure 8:
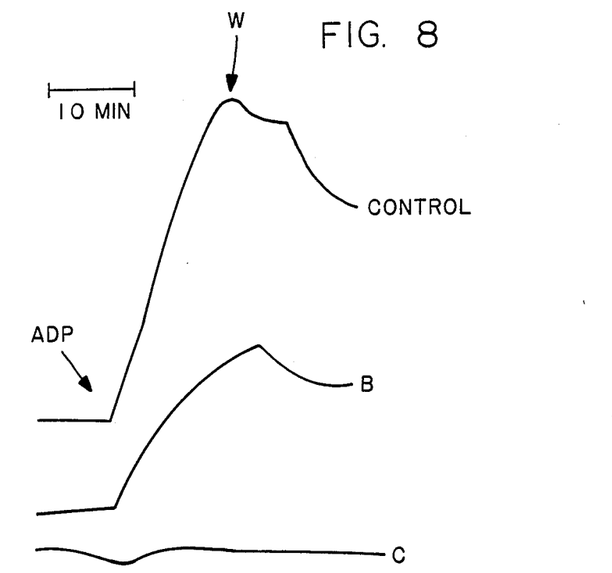
FIG. 8 is a profile of the contractile response absence of 1,3-bis-(2-trimethylpyrazinyl)propene (concentrations of (B) 20 μM and (C) 45 μM).

G. Observation: The effects of ADP (10 $\mu$M) on strip contractility are presented in FIG. 8. In the absence of inhibitor, the control (platelet strip in a bath solution of MK-H Working Solution) exhibits partial contraction with a rapid response to the challenge of ADP, and then washout ("W") after 10 minutes (FIG. 8, Control Curve). Washout refers to the procedure of washing the preparation repeatedly with a drug free solution (usually a saline solution) to terminate the contractile response returning to a baseline force. The control's contractile response to ADP demonstrates the presence of an intact receptor-control activity mechanism, whose outcome is platelet contraction. With 20 $\mu$M of the inhibitor compound of Example 5, the contraction is partially inhibited (FIG. 8, Curve B). The addition of 45 $\mu$M of inhibitor resulted in complete inhibition of contraction (FIG. 8, Curve C).

Figure 9:
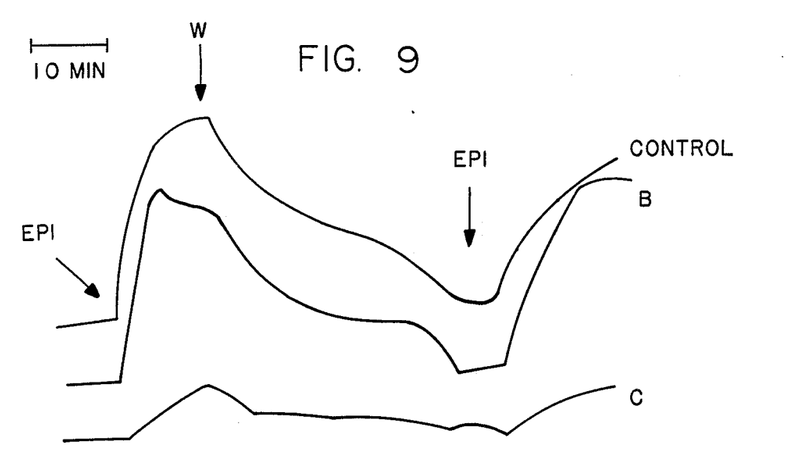
FIG. 9 is a profile of the contractile response of platelet strips to epinephrine (5.0 μM) in the presence or absence of 1,3-bis-(2-trimethylpyrazinyl)propene (concentrations of (B) 45 μM and (C) 90 μM).

The response of platelet strips to the contractile agonist epinephrine is illustrated in FIG. 9. In the absence of the inhibitor 5, the contraction response upon challenge by epinephrine resembles the response of the ADP challenged control as shown in FIG. 8. The presence of the Example 5 inhibitor compound of Example 5 at a concentration of 45 μM resulted in a response (FIG. 9, Curve B) that generated more inhibition as compared to the control (FIG. 9, Control Curve). An increase in inhibitor concentration (90 μM) resulted in a substantial decrease in contractile response (FIG. 9, Curve C).

Figure 10:
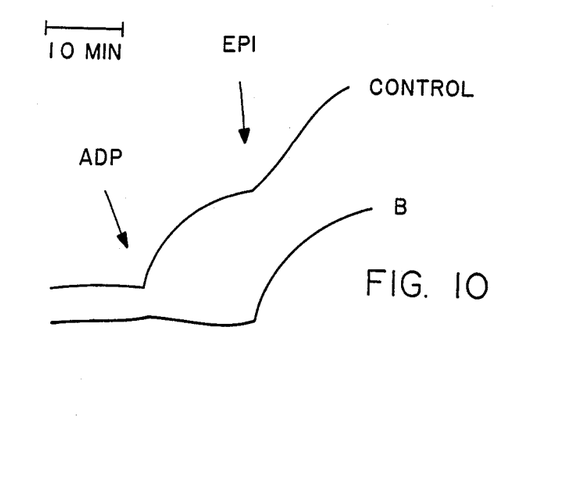
FIG. 10 is a profile of the contractile response of platelet strips to ADP (8.6 μM) and to further stimulation by epinephrine (8.6 μM), in the presence of 1,3-bis-(2-trimethylpyrazinyl)propene (62 μM).

In FIG. 10, the results of a sequential agonist addition on the force of contraction are presented. The presence of the Example inhibitor compound (62 μM) abolishes the response to ADP (8.6 μM) but not the response to the subsequent addition of epinephrine (8.6 μM) (FIG. 10, Curve B). Thus, the inhibition imparted by the compound of Example 5 is surmountable by the cumulative addition of agonist effecting different pathways. Without wishing to be bound by any theory, this suggests a specific action of the inhibitor compound of Example 5 on some receptormediated event as opposed as opposed to a non-specific effect on platelet contractility or metabolism.

Figure 11:
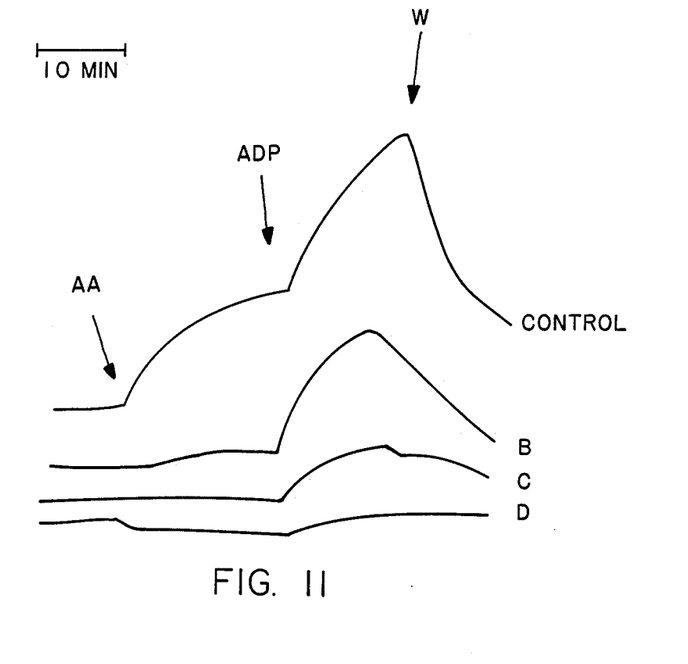
FIG. 11 is a profile of the contractile response of platelet strips to sodium arachidonate (20 μM) and to further stimulation by ADP (25 μM), in the presence or absence of 1,3-bis-(2-trimethylpyrazinyl)propene (concentrations of (B) 20 μM, (C) 45 μM and (D) 90 μM).

The effect of sodium arachidonate (20 μM) and the subsequent stimulation by ADP (25 μM) on the contractile response of the platelet-strip is presented in FIG. 11. The control strip shows a kinetic profile typical of arachidonate challenge, namely a slow and strong contraction that does not readily reverse upon washout. The contractual response is totally inhibited at all concentrations of the Example 5 compound (20 μM, 45 μM, 90 μM; Curves B, C and D, respectively). A graduated partial contractile response is evident when the preparations are further challenged by a supramaximal stimulus of ADP (25 μM). Without wishing to be bound by any theory, these observations suggest that the inhibitor compound of Example 5 antagonizes an event directly related to the prostaglandin and thromboxane pathway.

Figure 12:
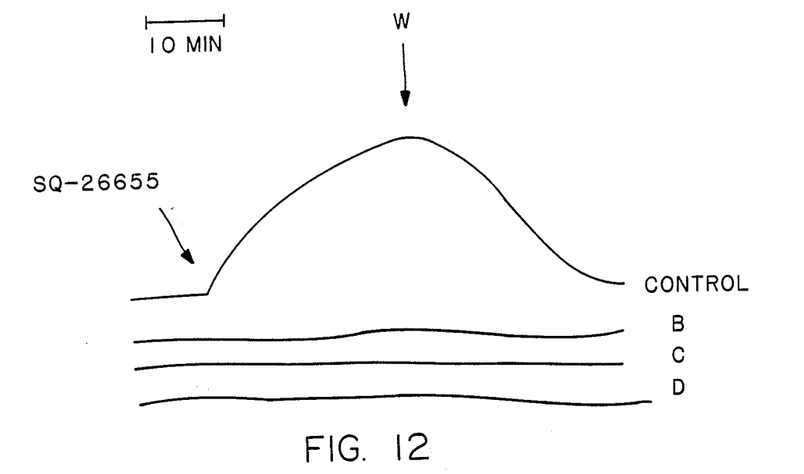
FIG. 12 is a profile of the contractile response of platelet strips to the thromboxane receptor agonist SQ-26655 (0.2 μM), in the presence or absence of 1,3-bis-(2-trimethylpyrazinyl)propene (concentrations of (B) 20 μM, (C) 45 μM and (D) 90 μM).

In order to delineate the effects of the Example 5 compound on a prostaglandin-mediated event, a thromboxane $A_2$ analog receptor agonist, SQ-26655(0.2 μM), was used to generate a contractile stimulus. As shown in FIG. 12, the control strip responded fully, exhibiting a slow, strong contraction wave similar to the control strip response to arachidonic acid shown in FIG. 11. In the presence of the Example 5 compound at various concentrations (20 μM, 45 μM, 90 μM; curves B, C, D, respectively), the contractile response to SQ-26655 was completely abolished.

Figure 13:
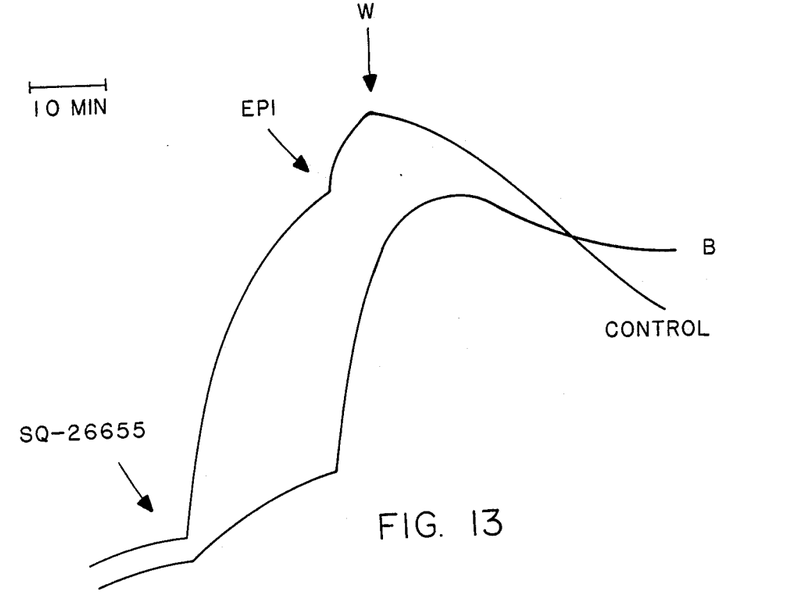
FIG. 13 is profile of the contractile response of platelet strips to a supramaximal stimulus by SQ-26655 (1.0 μM) and subsequent stimulation by epinephrine (8.6 μM) in the presence or absence of 1,3-bis-(2-trimethylpyrazinyl)propene (62 μM).

As shown in FIG. 13, the platelet-strip response was also inhibited when using a supramaximal concentration (1.0 μM) of SQ-26655. However, the inhibition of the response was overcome by the subsequent addition of 8.6 °M. of epinephrine (Curve B).

Bleeding Time Determinations

The method of Zawilska et al., *Br. J. Haemotol*, 50, 317 (1982) was employed to determine the effect of the inhibitor compound of Example 5 on in vivo platelet function. The bleeding time assay allows the direct measurement of platelet response to hemostasis. Furthermore, the following experiment will serve to illustrate the blood pressure reduction activity of the 2-substituted trimethylpyrazine derivatives of the present invention.

Male Wistar rats, weighing 360±/−40 grams, were fed on standard diets and then fasted 24 hours before experimentation. The rats were then anesthetized with pentobarbital and the areas around the sternum, femoral triangle, and mid-line abdomen were shaved. The animal was then placed on a heating pad at 37° C. and a tracheotomy tube was surgically inserted. The femoral vein was surgically exposed and intubated to allow intravenous dosage of the inhibitor compound of Example 5 and maintenance of anesthetic. The carotid artery was intubated and connected to an instantaneous blood pressure transducer allowing the monitoring of hemodynamic changes. Once intubated and stabilized, a midline incision was made and the small intestine was draped over a plastic plate. Using an Olympus Microscope at a magnification of 63× or 100×, the mesenteric arteries were observed. Control animals were injected with an equal volume of a saline solution prior to any determination. Five minutes after the injection, the mesenteric arteries were cut and the bleeding time determined. One group of test animals was injected intravenously with the inhibitor compound of Example 5 at a dosage of 25 mg/kg. Another group of test animals was injected intravenously once a day for 7 days with 1 mg/kg. The results of these experiments are presented in FIGS. 14 and 15.

Figure 14:
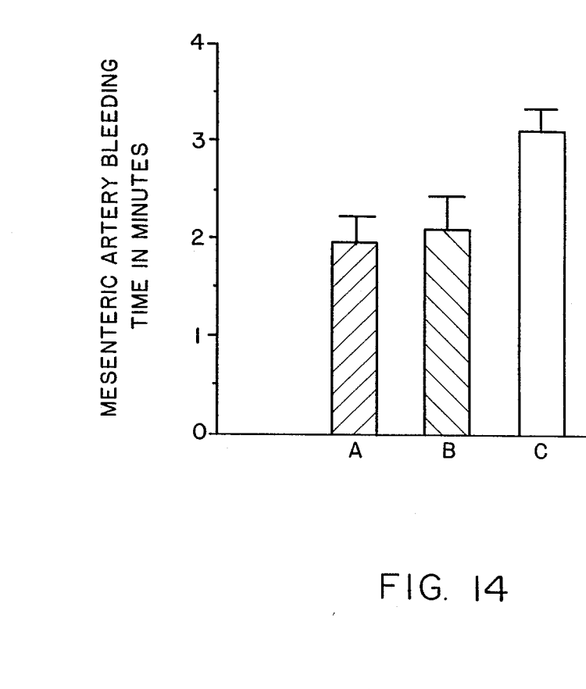
FIG. 14 is a graph showing the effect of 1,3-bis-(2-trimethylpyrazinyl)propene on mesenteric artery bleeding-time of male Wistar rats after acute and chronic administration.
Figure 15A:
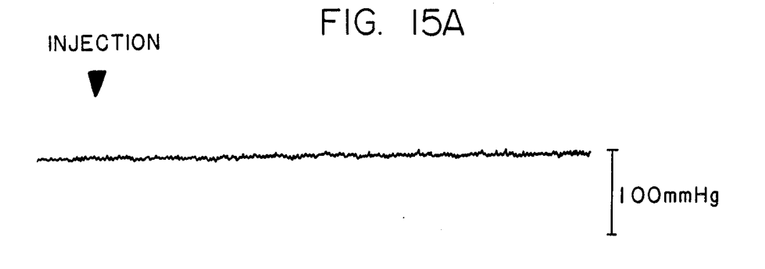
Figure 15B:
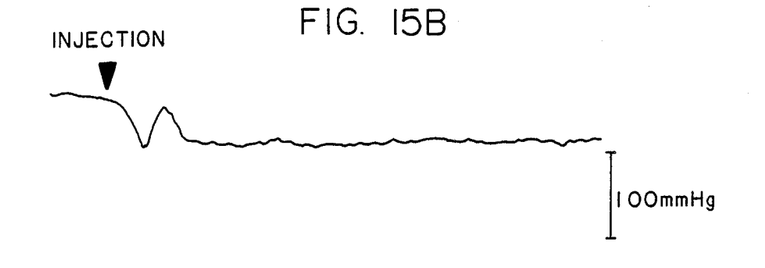
Figure 15C:
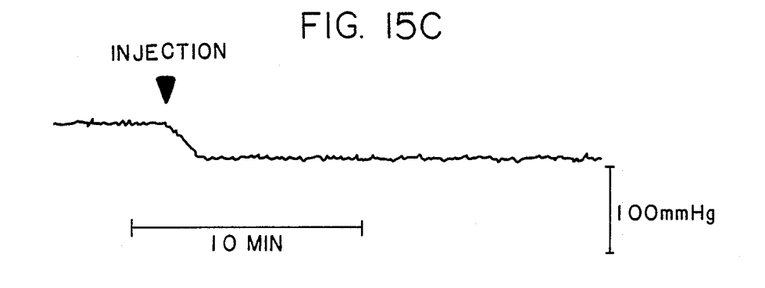

The effect of the Example 5 compound on mesenteric artery bleeding time after acute and chronic administration is shown in FIG. 14. The control group had a bleeding time of about 2 minutes (Bar A). The group of test animals given acute injections of 25 mg/kg of Example 5 compound had bleeding times of about 2.2 minutes (Bar B). The group of test animals subjected to chronic injections (1 mg/kg a day for 7 days) exhibited bleeding times of about 3.1 minutes.

As shown in FIG. 15, a 10 to 20 minute decrease in blood pressure was observed in the test animals injected with 25 mg/kg of the inhibitor compound of Example 5 (see Tracing B). The control group of test animals were merely injected with Ringer's solution prior blood pressure measurements (Tracing A). The test animals subjected to chronic injections of 1 mg/kg per day for 7 days exhibited small decreases in blood pressure which lasted for 10 to 15 minutes (Tracing C).

The decrease in blood pressure observed after the injections of the inhibitor compound of Example 5 indicates that the compound is effective as a promoter of blood pressure reduction.

The increase in the in vivo bleeding times observed after chronic administration of low doses of the Example 5 compound indicates that the compound maintains pharmacological activity in a whole animal system and provides an effect consistent with the in vitro observations (inhibition of platelet aggregation assay and platelet strip assay).

The compounds of the present invention may be administered to mammals parenterally in combination with any inert pharmaceutically acceptable carrier. Liquid carriers for injectable preparations include water, saline solution, dextrose solution and the like.

The quantity of the active ingredient administered can vary over a wide range depending upon the mode of administration, the size and weight of the subject and whether the nature of the treatment is prophylactic or therapeutic in nature. Dosages from about 0.1 to about 50 mg/kg may be administered as needed for inhibiting blood platelet aggregation and/or promoting blood pressure reduction in mammals, the preferable dosage being from about 1 to about 25 mg/kg.

The present invention may be embodied in other specific forms without departing from the spirit or essential attributes thereof and, accordingly, reference should be made to the appended claims, rather than to

We claim:
1. A compound having the formula:

wherein R is selected from the group consisting of alkylamino containing from 1 to 4 carbon atoms 4-methyl-1-piperazinyl, piperidino, and 2-trimethylpyrazinepropenyl.

2. A compound according to claim 1 wherein the compound is 3,5,6-trimethylpyrazinylmethyl-N-pentylamine.

3. A compound according to claim 1 wherein the compound is 2-methylene(4'-methylpiperazinyl-1')-3,5,6-trimethylpyrazine.

4. A compound according to claim 1 wherein the compound is 2-methylene(piperidinyl-1')-3,5,6-trimethylpyrazine.

5. A compound according to claim 1 wherein the compound is 1,3-bis-(2-trimethylpyrazinyl)propene.

6. A method for inhibiting blood platelet aggregation in mammals which comprises administering to such mammals an amount of a compound of the formula wherein R is selected from the group consisting of alkylamino containing from 1 to 4 carbon atoms, 4-methyl-1-piperazinyl, piperidino, morpholino and 2-trimethylpyrazinepropenyl, said amount being effective to inhibit blood platelet aggregation.

7. A method according to claim 6 wherein the compound is 3,5,6-trimethylpyrazinylmethyl-N-pentylamine.

8. A method according to claim 6 wherein the compound is 2-(4'-methylpiperazinyl-1')-3,5,6-trimethylpyrazine.

9. A method according to claim 6 wherein the compound is 2-(piperidinyl-1')-3,5,6-trimethylpyrazine.

10. A method according to claim 6 wherein the compound is 2-(morpholino-1')-3,5,6-trimethylpyrazine.

11. A method according to claim 6 wherein the compound is 1,3-bis-(2-trimethylpyrazinyl)propene.

12. A method for promoting blood pressure reduction in mammals which comprises administering to such mammal an amount of a compound of the formula.

wherein R is selected from the group consisting of alkylamino containing from 1 to 4 carbon atoms, 4-methyl-1-piperazinyl, piperidino, morpholino and 2-trimethylpyrazinepropenyl, said amount being effective to promote blood pressure reduction.

13. A method according to claim 12 wherein the compound is 3,5,6-trimethylpyrazinylmethyl-N-pentylamine.

14. A method according to claim 12 wherein the compound is 2-(4'-methylpiperazinyl-1')-3,5,6-trimethylpyrazine.

15. A method according to claim 12 wherein the compound is 2-(piperidinyl-1')-3,5,6-trimethylpyrazine.

16. A method according to claim 12 wherein the compound is 2-(morpholino-1')-3,5,6-trimethylpyrazine.

17. A method according to claim 12 wherein the compound is 1,3-bis-(2-trimethylpyrazinyl)propene.

18. A pharmaceutical composition for inhibiting blood platelet aggregation or promoting blood pressure reduction in mammals comprising, in combination with a pharmaceutically acceptable carrier, an effective amount of a compound having the formula wherein R is selected from the group consisting of alkylamino containing from 1 to 4 carbon atoms, 4-methyl-1-piperazinyl, piperidino, and 2-trimethylpyrazinepropenyl, said amount being effective to inhibit blood platelet aggregation or promote blood pressure reduction.

19. A composition according to claim 18 wherein the compound is 3,5,6-trimethylpyrazinylmethyl-N-pentylamine.

20. A composition according to claim 18 wherein the compound comprises 2-methylene(4'-methylpiperazinyl-1')-3,5,6-trimethylpyrazine.

21. A composition according to claim 18 wherein the compound comprises 2-methylene(piperidinyl-1')-3,5,6-trimethylpyrazine.

22. A composition according to claim 18 wherein the compound is 1,3-bis-(2-trimethylpyrazinyl)propene.

* * * * *